July 28, 1964 P. DOT Plant Pat. 2,430
ROSE PLANT
Filed Sept. 26, 1963
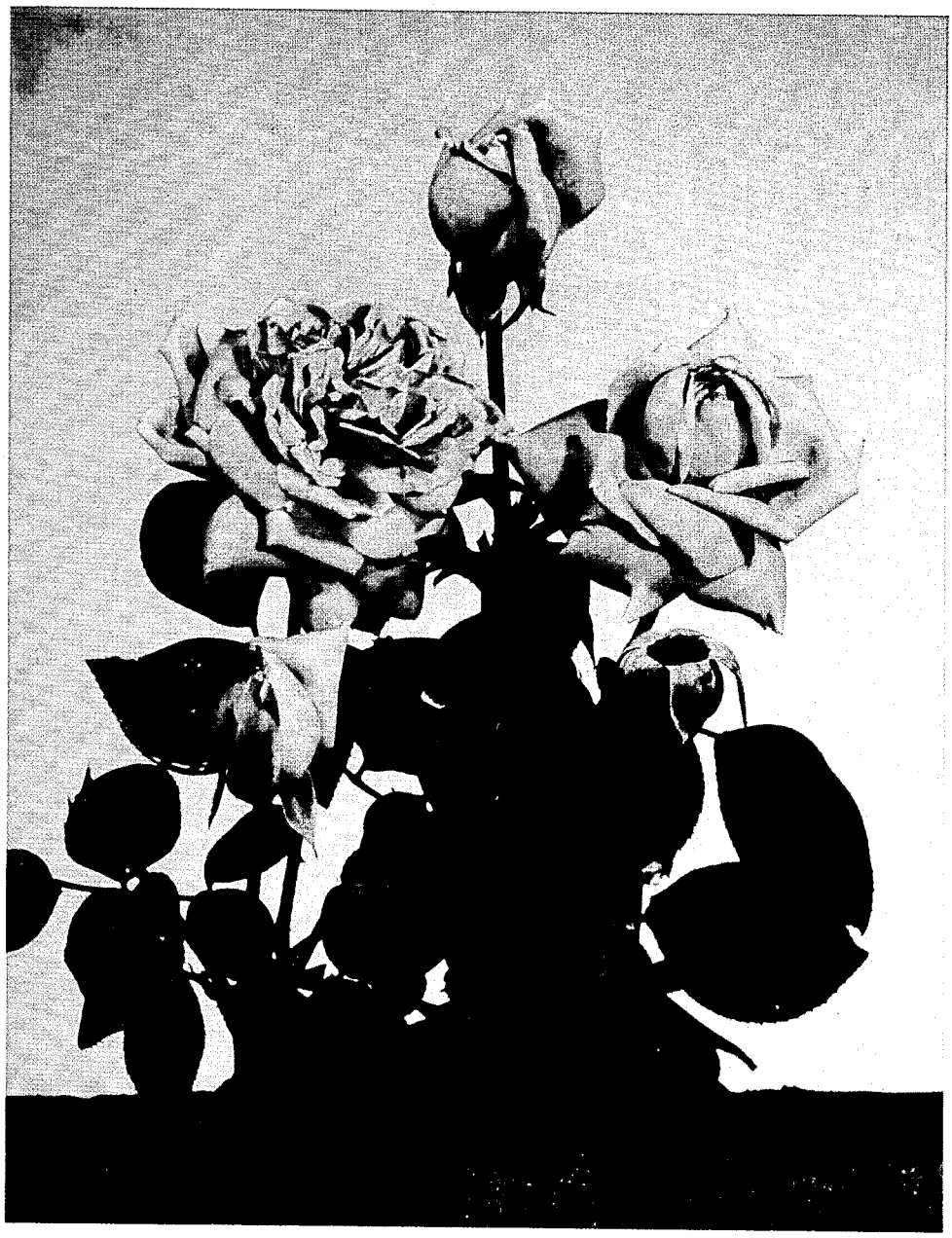
Inventor.
Pedro Dot
By: Robb & Robb
Attorneys.

United States Patent Office

Plant Pat. 2,430
Patented July 28, 1964

2,430
ROSE PLANT

Pedro Dot, Barcelona, Spain, assignor to The Conard-Pyle Company, West Grove, Pa., a corporation of Pennsylvania Filed Sept. 26, 1963, Ser. No. 311,931
1 Claim. (Cl. Plt.—11)

The present invention relates to a new and distinct variety of rose plant of the hybrid tea class, which was originated by me by crossing the variety "Grey Pearl" (U.S. Plant Patent No. 680) with the variety "Lila Vidri" (unpatented).

As the result of this breeding, I have produced a new and improved rose variety which is distinguished from its parents, as well as from all other varieties of which I am aware, as evidenced by the following unique combination of characteristics which are outstanding therein:

(1) A generally compact and moderately tall habit of growth;

(2) A good and continuous flowering habit, with the flowers being borne in clusters of several to a stem;

(3) Good flower petalage, usually ranging from 23 to 28 petals;

(4) A Deep Lilac general color tonality of the flowers which is maintained from the opening stage to maturity with only slight fading; and (5) A moderate centifolia flower fragrance.

Asexual reproduction of the new variety by budding, as performed in Spain and at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, which color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—"Grey Pearl."

*Pollen parent.*—"Lila Vidri."

Propagation: Holds its distinguishing characteristics through succeeding propagations by budding.

*Flower*

Locality where grown and observed: West Grove, Pennsylvania, U.S.A.

Flower borne: Sometimes singly, but mostly several to a stem; on stems of medium length and normal strength.

Quantity of bloom: Free, outdoors.

Continuity: Continuous.

Fragrance: Moderate. Nature—centifolia.

Bud:

*Peduncle.*—Medium length; medium caliper; erect; medium roughness; with medium number of brown hairs. Color—green, overlaid with bronze.

*Before calyz breaks.*—Size—medium. Form—short; roundly ovoid; with a conspicous neck; with foliaceous appendages on the surface of the bud; with bristle-like foliaceous parts extending beyond the tip of the bud equal to ¼ or less of its length.

*As calyx breaks.*—Color—Erythrite Red, Plate 0027.

*As first petal opens.*—Size—medium. Form—pointed ovoid. Color: outside—near Uranium Green, Plate 63/3 at base, becoming progressively shaded with Petunia Purple, Plate 32/3 toward the margin of the petal, with petals sometimes being irregularly blotched with deeper shades of latter color; inside—Petunia Purple, Plate 32/3, with Uranium Green, Plate 63/3 at base.

*Opening.*—Opens up well.

Bloom:

*Size (when fully open).*—Medium; from 3 inches to 3½ inches.

*Petalage.*—Double; from 23 to 28 petals; arranged regularly.

*Form.*—High-centered at first, but becoming shallow cupped; petals being at first from flat to slightly rolled outward, but becoming loosely rolled outward at maturity.

Petals:

*Texture.*—Medium.

*Appearance.* — Inside — satiny. Outside — shiny-satiny.

*Shape.*—Outer petals—orbicular, with apex irregularly notched. Intermediate petals—orbicular. Inner petals—irregular.

This description of a newly opened flower was made from a rose grown outdoors during the month of August at West, Groove, Pennsylvania, U.S.A.:

*Color.*—Outer petal: outside surface—Rose Purple, Plate 533/2, becoming tinted over basal half of petal with Uranium Green, Plate 63/3 which reaches its maximum intensity at point of attachment; inside surface—Pansy Violet, Plate 033/3, blending with and changing to Primrose Yellow, Plate 601/3 over basal ¼ of the petal. Intermediate petal: outside surface—Pastel Mauve, Plate 433/1, becoming tinted with and changing to Sap Green, Plate 62/3 at point of attachment; inside surface—Pansy Violet, Plate 033/3, becoming blended with Primrose Yellow, Plate 601/3 over basal ¼ of petal, and with point of attachment being Primrose Yellow, Plate 601/3. Inner petal: outside surface—Pastel Mauve, Plate 433, becoming lighter over basal ¼ of petal and changing gradually to Sap Green, Plate 62/3 at point of attachment; inside surface—Pansy Violet, Plate 033/3, often with a streak of Primrose Yellow, Plate 601/3 running from the point of attachment to the apex of the petal.

This description was made from a rose that was open for three days outdoors during the month of August at West Groove, Pennsylvania, U.S.A.:

*Color.*—Outer petal: outside surface—near Phlox Purple, Plate 632/3, gradually becoming Uranium Green, Plate 63/3 near base of petal; inside surface—Rose Purple, Plate 533/1, grading to Uranium Green, Plate 63/3 at base of petal. Inner petal; outside surface—near Phlox Purple, Plate 632/3, with basal area of petal being Uranium Green of a tint slightly lighter than Plate 63/3; inside surface—Rose Purple, Plate 533/1, grading to Uranium Green, Plate 63/3 over the basal ¼ of petal.

*General color effect.*—Newly opened flower—Pansy Violet, Plate 033/3. Three days open—Rose Purple, Plate 533/1.

*Behavior.*—Drop off cleanly.

*Flower longevity.*—On bush in garden—3 days in August. Cut roses grown outdoors and kept at living room temperatures—3 days in August.

*Reproductive Organs*

Stamens: Many; arranged regularly about pistils; mixed with petaloids.
Fliaments: Many; medium length; most with anthers. Color—pale yellow.
Anthers: Medium size; all open at once; occasionally an anther fused with a petaloid. Color—yellow.
Pollen: Abundant. Color—gold.
Pistils: Medium number.
Styles: Uneven; medium length; medium caliper; bunched.
Stigma: Color—white-yellow.
Ovaries: All enclosed in receptacle.
Hips: Globular; with inconspicuous neck; smooth; medium thin walls; fleshy. Color—green.
Sepals: Permanent; medium length; spear-shaped.
Seeds: Many; medium size.

*Plant*

Foliage:

*Leaves.*—Compound of 3 or 5 leaflets; normal abundance; medium size; moderately thin; glossy.

*Leaflets.*—Shape—oval. Apex—acute. base—obtuse. Margin—simply serrate.

*Color.*—Mature: upper surface—Spinach Green, Plate 0960; under surface—Lavender Green, Plate 000761. Young: upper surface—Spinach Green, Plate 0960/1, overlaid with Erythrite Red, Plate 0027; under surface—Erythrite Red, Plate 0027, overlying Lettuce Green, Plate 861.

*Rachis (the supporting stem of the compound leaf).*—Medium caliper. Upper side—grooved; hairy. Under side—sparsely prickly.

*Stipules.*—Medium length; moderately narrow; with short points turning out at an angle of more or less 45°.

*Disease resistance.*—Comparable to that of the average variety grown under the same cultural conditions at West Grove, Pennsylvania, U.S.A.

Growth:

*Habit.*—Bushy; much-branched.

*Growth.*—From moderate to free.

*Canes.*—Medium caliper.

*Main stems.*—Dull. Color—Spinach Green, Plate 0960. Prickles—several; pointed slightly downward; color—brown. Hairs—none.

*Branches.*—Dull. Color—Spinach Green, Plate 0960. Prickles—several; pointed slightly downward; color—green. Hairs—none.

*New shoots.*—Dull. Color—Fern Green, Plate 0862, lightly overlaid with Erythrite Red, Plate 0027/1. Prickles—several; color—reddish brown. Hairs—few; color—reddish brown.

I claim:

A new and distinct variety of rose plant of the hybrid tea class, substantially as herein shown and described, characterized particularly as to novelty by the unique combination of a generally compact and moderately tall habit of growth, a good and continuous flowering habit, with the flowers generally being borne in clusters of several to a stem, good flower petalage, a Deep Lilac general color tonality of the flowers which is maintained from the opening stage to maturity with only slight fading, and a moderate centifolia flower fragrance.

No references cited.